US00PP34839P2

(12) United States Plant Patent
Growns

(10) Patent No.: US PP34,839 P2
(45) Date of Patent: Dec. 13, 2022

(54) ***SCAEVOLA* PLANT NAMED 'LUEDANSCA'**

(50) Latin Name: *Scaevola crassifolia*
Varietal Denomination: Luedansca

(71) Applicant: Botanic Gardens and Parks Authority, Perth (AU)

(72) Inventor: Digby James Growns, Perth (AU)

(73) Assignee: Botanic Gardens and Parks Authority, Perth (AU)

( * ) Notice: Subject to any disclaimer, the term of this patent is extended or adjusted under 35 U.S.C. 154(b) by 0 days.

(21) Appl. No.: 17/482,788

(22) Filed: Sep. 23, 2021

(51) Int. Cl.
*A01H 6/00* (2018.01)
*A01H 5/02* (2018.01)

(52) U.S. Cl.
USPC ..... Plt./363

(58) Field of Classification Search
USPC ..... Plt./363
CPC ..... A01H 6/00; A01H 5/02
See application file for complete search history.

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Scaevola* plant, referred to by its cultivar name, 'Luedansca', is disclosed. The new variety displays true blue colored flowers and medium to dark green colored foliage. Attractive moderately vigorous vegetative is formed. The growth habit is compact and mounded. The new variety is well suited for providing attractive ornamentation in the landscape.

2 Drawing Sheets

Figure 1:
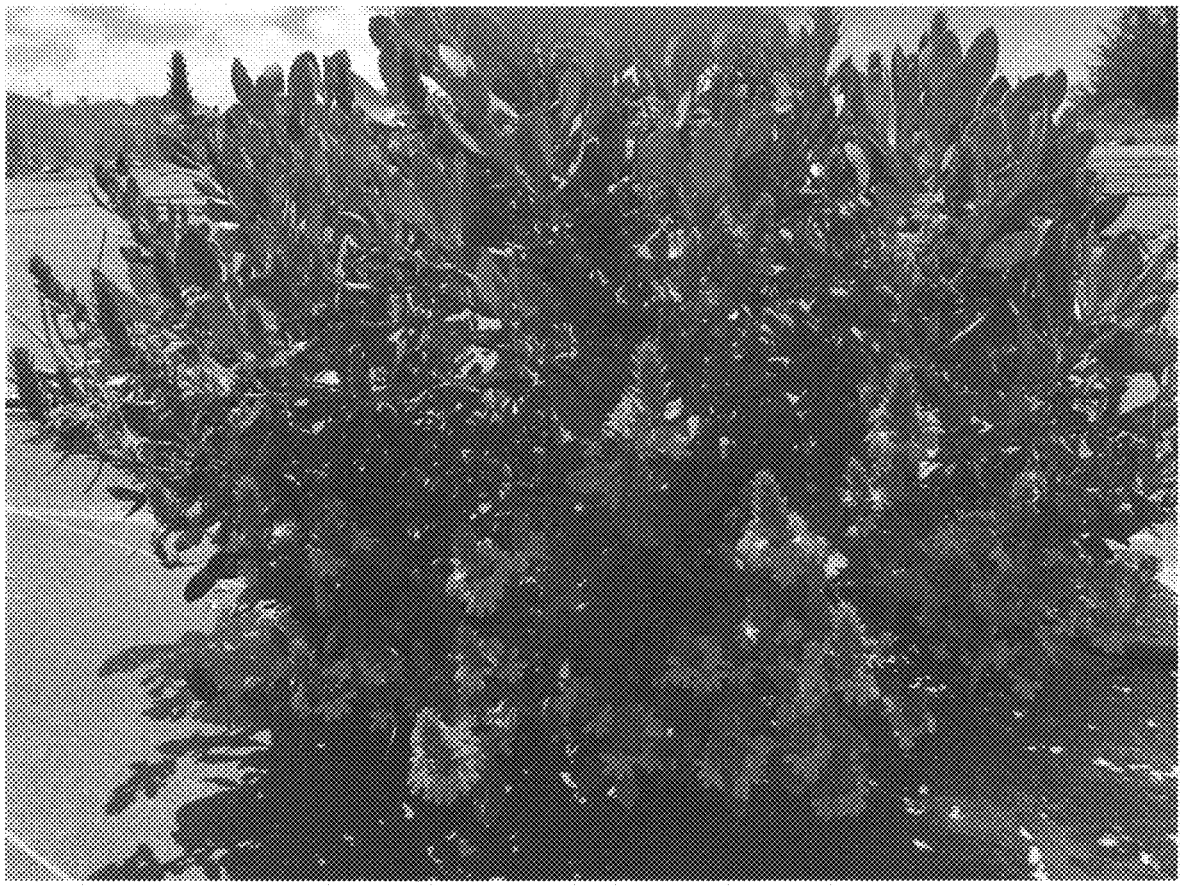

Latin name of genus and species of plant claimed: *Scaevola crassifofia.*
Variety denomination: 'Luedansca'.

BACKGROUND OF THE INVENTION

The new variety of *Scaevola crassifolia* plant originated in a controlled breeding program in Perth, Western Australia during August 2015. The objective of the breeding program was the development of new ornamental Australian plant varieties. The new cultivar was created by cross-pollination wherein two parents were crossed which previously had been studied in the hope that they would contribute the desired characteristics. The female parent (i.e., the seed parent) was an unnamed breeder seedling variety (not patented). The male parent (i.e., the pollen parent) was the 'Benara' variety (not patented).

The parentage of the new variety can be summarized as follows:

unnamed breeder seedling x 'Benara'

The new cultivar was discovered and selected as a single flowering plant from the progeny resulting from the above-stated cross-pollination during August 2016 in a controlled environment in Perth, Western Australia. Selective study resulted in the identification of a single plant of the new variety.

The new variety has been found to undergo asexual propagation by terminal stem cuttings. Asexual propagation by terminal stem cuttings in Perth, Western Australia since September 2016 has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of *Scaevola* plant of the present invention:

(a) forms true blue colored flowers,
(b) displays medium to dark green colored foliage, and
(c) exhibits a moderately vigorous, compact, mounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed breeding seedling female parent (i.e., the seed parent) displays pale blue colored flowers and exhibits an upright to bushy growth habit, whereas the new variety displays true blue colored flowers, which are darker in color compared to the female parent and exhibits a more compact, mounded growth habit compared to the female parent. The male parent 'Benara' variety (i.e., the pollen parent) displays an upright to bushy growth habit, whereas the new variety displays a compact, mounded growth habit.

The new variety can also be distinguished from other similar varieties that are commercially available. For instance, the new variety of the present invention can readily be distinguished from the straight species *Scaevola crassifolia* (not patented), as the new cultivar displays a denser branching habit, produces stronger blue flower clusters that rebloom with more flowers, and exhibits more flowers per plant compared to plants of the straight species *Scaevola crassifolia.*

The new variety has been named 'Luedansca'.

The new variety was first offered for sale or first sold on May 17, 2021 in California by the inventor or by another who obtained the new variety directly or indirectly from the inventor.

BRIEF DESCRIPTION OF THE PHOTOGRAPH

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Luedansca' variety. The plants were grown in three-gallon pots for approximately three years at Arroyo Grande, Calif. Photographs were taken in April 2021.

FIG. 1—illustrates a specimen of the plant displaying the overall growth and flowering habit—side view.

Figure 2:
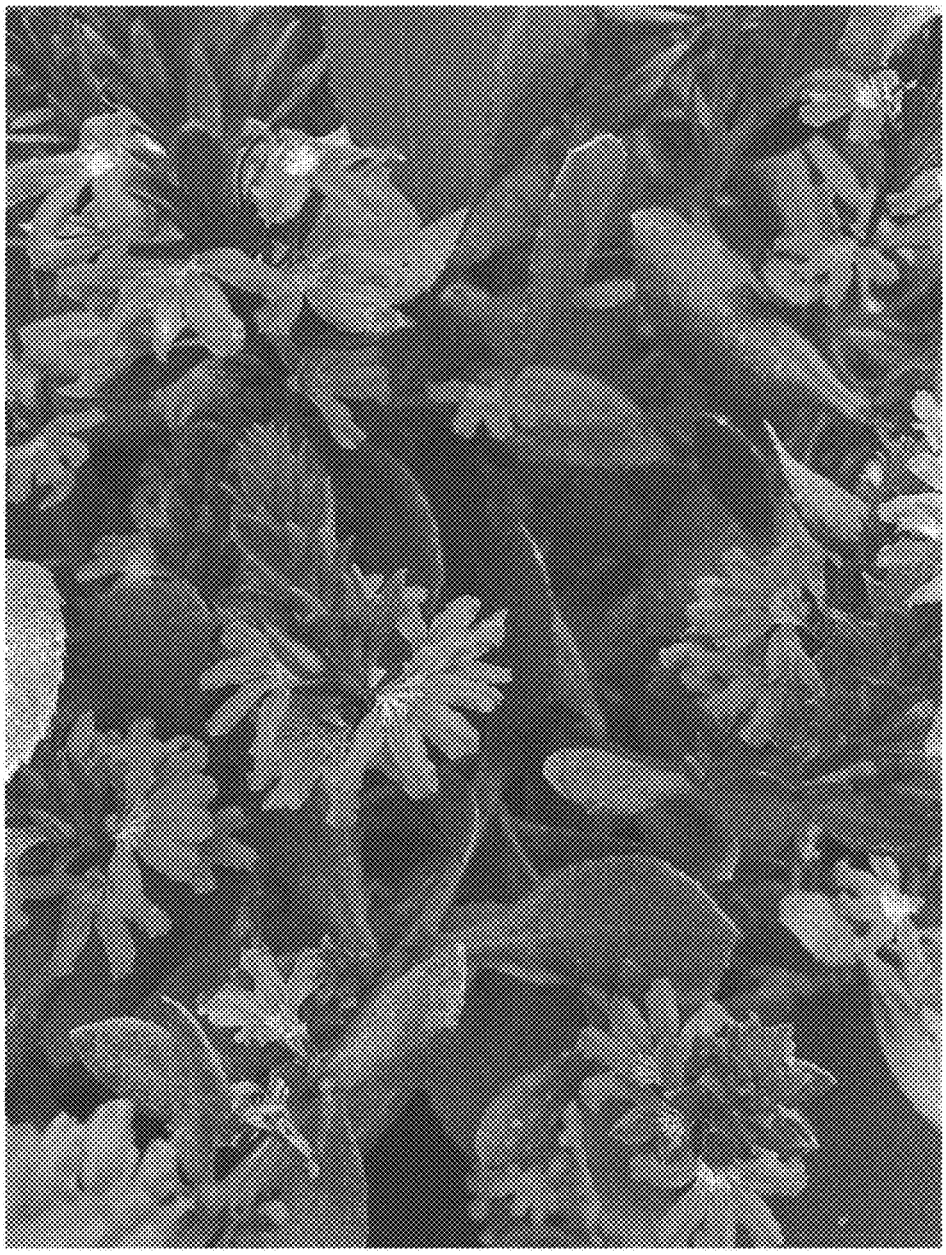

FIG. 2—illustrates specimens of flowers—close-up view.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The description is based on the observation of a two-year-old specimen of the new variety.

Propagation:

*Type cutting*.—Terminal stem, softwood cuttings.

*Time to initiate roots*.—Approximately 4 weeks on average.

*Time to produce a rooted cutting*.—Approximately 8 weeks on average.

*Root description*.—Fibrous.

*Rooting habit*.—Very dense.

Plant:

*Habit*.—Moderately vigorous, compact, mounded growth habit.

*Commercial crop time*.—Approximately 8 weeks to finish in a three-gallon container on average.

*Hardiness*.—USDA Zones 8-10.

*Size*.—Approximately 40.0 cm in height on average; and approximately 65.0 cm in width on average.

Branches:

*Branching habit*.—Freely branching, secondary stems form uniformly around main central stem.

*Quantity of branches*.—Approximately 20 on average.

*Strength*.—Very strong.

*Aspect*.—Secondary stems form at a 70° angle to main stems.

*Main branch*.—Length: approximately 40.0 cm on average. — diameter: approximately 1.0 cm on average.

*Lateral branches*.—Length: approximately 36.0 cm on average. — diameter: approximately 5.0 mm on average.

*Central internode*.—Length: approximately 2.0 cm to 3.0 cm on average.

*Stem texture*.—Moderately rough, becoming woody with age.

*Stem color*.—Commonly between near Yellow-Green Group 144A to Yellow-Green Group 146A.

Foliage:

*Leaf fragrance*.—Moderately herbal to musky scent.

*Leaf form*.—Simple.

*Leaf arrangement*.—Alternate.

*Leaf shape*.—General: oblanceolate. — margin: serrated. — apex: acuminate. — base: attenuate.

*Venation pattern*.—Pinnate.

*Size*.—Length of mature leaf: approximately 5.0 cm to 6.0 cm on average. — width of mature leaf: approximately 2.0 cm on average.

*Texture*.—Upper and lower surfaces: moderately rough and somewhat leathery.

*Color*.—Upper surface of developing and fully expanded leaves: commonly near Yellow-Green Group 147A with venation of near Yellow-Green Group 147A. — lower surface of developing and fully expanded leaves: commonly near Yellow-Green Group 147B with venation slightly darker than Yellow-Green Group 144A.

*Petiole*.—Length: approximately 0.8 cm to 1.0 cm on average. — diameter: approximately 2.0 mm to 3.0 mm on average. — texture: glabrous. — color: commonly near Yellow-Green Group 147B.

Flower:

*Type and shape*.—Zygomorphic, semi-circular, fan-shaped flowers with five petals fused at the base to form a tubular flower throat; flower throats open along the upper surface exposing reproductive organs; flowers not persistent.

*Fragrance*.—None detected.

*Arrangement and quantity*.—Solitary flowers arise from leaf axils with one flower per axil. Flowers held outwardly on upturned lateral apices. Freely flowering, typically about six to ten open flowers per inflorescence.

*Buds*.—Shape: lanceolate. — length: approximately 8.0 mm on average. — diameter: approximately 2.0 mm on average. — color: commonly near Green Group 138B becoming closer to Yellow-Green Group 144A overlain with near Greyed-Purple Group 187C with development.

*Perianth*.—Aspect: fan-shaped, flat. — length, fan: approximately 1.6 cm on average. — width, fan: approximately 1.5 cm on average. — flower throat diameter: approximately 2.5 mm on average. — flower tube length: approximately 1.0 cm on average. — flower tube diameter, base: approximately 1.0 mm on average.

*Petals*.—Quantity: five, fused at base. — shape: lanceolate to ovate. — apex: cuspidate. — margin: entire. — length, above tube: approximately 1.0 cm on average. — width, above tube: approximately 4.0 mm on average. — texture, upper and lower surfaces: smooth; flower throat, whiskered. — color when opening, upper surface: commonly near Violet-Blue Group 96B. — color when opening, lower surface and tube: commonly near Violet-Blue Group 96C. — color when fully opened, upper surface: commonly near Violet-Blue Group 96B; venation is commonly near Violet-Blue Group 90D, color becoming closer to Violet-Blue Group 96B with development. — color fully opened, lower surface: commonly near Violet-Blue Group 96C and venation is commonly near Violet Group 85D; throat is commonly near Yellow Group 6B and venation is commonly near Purple Group N79A; tube is commonly near Yellow-Green Group 145A and venation is commonly near Brown Group 200C.

*Sepals*.—Quantity and arrangement: one large sepal, two smaller sepals lateral to larger sepal. — length: larger sepal is approximately 9.0 mm to 1.0 cm; lateral sepals are approximately 7.5 mm on average. — width: larger sepal is approximately 5.9 mm on average; lateral sepals are approximately 1.2 mm on average. — shape: larger sepal is ovate to rhomboid; lateral sepals are acicular, needle-like. — apex: acute. — margin: entire. — texture, upper and lower surfaces: leathery, slightly pubescent. — color, upper surface: commonly near Green Group 137B. — color, lower surface: commonly near Green Group 137C.

*Reproductive organs*.—Stamen quantity per flower: about five. — anthers shape: ovate. — anthers length: approximately 1.0 mm on average. — anthers diameter: approximately 1.0 mm on average. — anthers color: commonly near Yellow-Orange Group 18B. — filament length: approximately 3.0 mm on average. — pollen amount: sparse. — pollen color: commonly near Yellow-Orange Group 18B. — pistil quantity per flower: one. — pistil length: approximately 6.0 mm on average. — style length: approximately 5.0 mm on average. — style color: towards the base is commonly near Yellow-Green Group 147D; towards the apex is commonly near Greyed-Purple Group 187A. — stigma shape: elongate. — stigma color: commonly near White Group 155A to Green-White Group 157A; pubescence is commonly near Greyed-Purple Group 187A. — ovary color: commonly near Yellow-Green Group 144A.

*Seed/fruit*.—Seed and furth production has not been observed.

Development:

*Flowering time*.—Plants flower heavily in the spring and sparingly through the warm season; flowers typically last about one week on the plant.

*Disease/pest resistance*.—Plants of the new variety have not been noted to be resistant to pathogens and pests common to *Scaevola*.

The new 'Luedansca' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Scaevola* plant named 'Luedansca' characterized by the following combination of characteristics:

(a) forms true blue colored flowers, (b) displays medium to dark green colored foliage, and (c) exhibits a moderately vigorous, compact, mounded growth habit;

substantially as herein shown and described.

* * * * *